US012564592B1

(12) United States Patent
Raichur et al.

(10) Patent No.: US 12,564,592 B1
(45) **Date of Patent: *Mar. 3, 2026**

(54) INJECTABLE LEUCOVORIN FORMULATIONS AND METHODS OF PREPARING SAME

(71) Applicant: Riconpharma LLC, Denville, NJ (US)

(72) Inventors: Vinay Sudhindra Raichur, Hyderabad (IN); Vijaya Kumar Thota, Hyderabad (IN); Svb Janardhan Garikipati, Hyderabad (IN); Praveen Reddy Billa, Flanders, NJ (US); Mukteeshwar Gande, Monroe, NJ (US)

(73) Assignee: Riconpharma LLC

( * ) Notice: Subject to any disclaimer, the term of this patent is extended or adjusted under 35 U.S.C. 154(b) by 0 days.

This patent is subject to a terminal disclaimer.

(21) Appl. No.: 19/268,785

(22) Filed: Jul. 14, 2025

Related U.S. Application Data

(63) Continuation-in-part of application No. 18/991,888, filed on Dec. 23, 2024.

(51) Int. Cl.

| | |
|---|---|
| ***A61K 31/519*** | (2006.01) |
| ***A61J 1/14*** | (2023.01) |
| ***A61K 9/00*** | (2006.01) |
| ***A61K 31/513*** | (2006.01) |
| ***A61K 47/02*** | (2006.01) |
| ***A61K 47/18*** | (2017.01) |
| ***A61K 47/40*** | (2006.01) |

(52) U.S. Cl.
CPC ............... *A61K 31/519* (2013.01); *A61J 1/14* (2013.01); *A61K 9/0019* (2013.01); *A61K 31/513* (2013.01); *A61K 47/02* (2013.01); *A61K 47/18* (2013.01); *A61K 47/40* (2013.01)

(58) Field of Classification Search
CPC .. A61K 31/519; A61K 31/513; A61K 9/0019; A61K 47/02; A61K 47/18; A61K 47/40; A61J 1/14
USPC ........................................................ 424/400
See application file for complete search history.

(56) References Cited

U.S. PATENT DOCUMENTS

| | | | | |
|---|---|---|---|---|
| 4,931,441 A | 6/1990 | Lawrence | | |
| 2009/0221594 A1 * | 9/2009 | Chen | A61K 31/525 514/249 | |

FOREIGN PATENT DOCUMENTS

| | | | | |
|---|---|---|---|---|
| EP | 0416232 A2 | 3/1991 | | |
| EP | 0427078 A1 | 5/1991 | | |
| EP | 1640008 A1 | 3/2006 | | |
| WO | WO-2008106721 A1 * | 5/2019 | A61K 31/505 | |

* cited by examiner

*Primary Examiner* — Michael G. Hartley
*Assistant Examiner* — Sean R Donohue
(74) *Attorney, Agent, or Firm* — The Belles Group, P.C.

(57) ABSTRACT

Described herein are clear, stable aqueous formulations comprising—in relevant part—leucovorin calcium; substituted cyclodextrins, specifically betadex suclfobutyl ether cyclodextrin (SBE-β-CD) or hydroxypropyl beta cyclodextrin (HP-β-CD), designed for parenteral administration. The formulations are designed to effectively prevent drug crystallization and particulate matter formation, addressing major stability challenges associated with existing products. These advancements not only improve the safety and efficacy of leucovorin calcium for intravenous administration but also facilitate compliance with regulatory standards, providing a reliable therapeutic option for patients. Methods of making and using these formulations are also described herein.

20 Claims, 1 Drawing Sheet

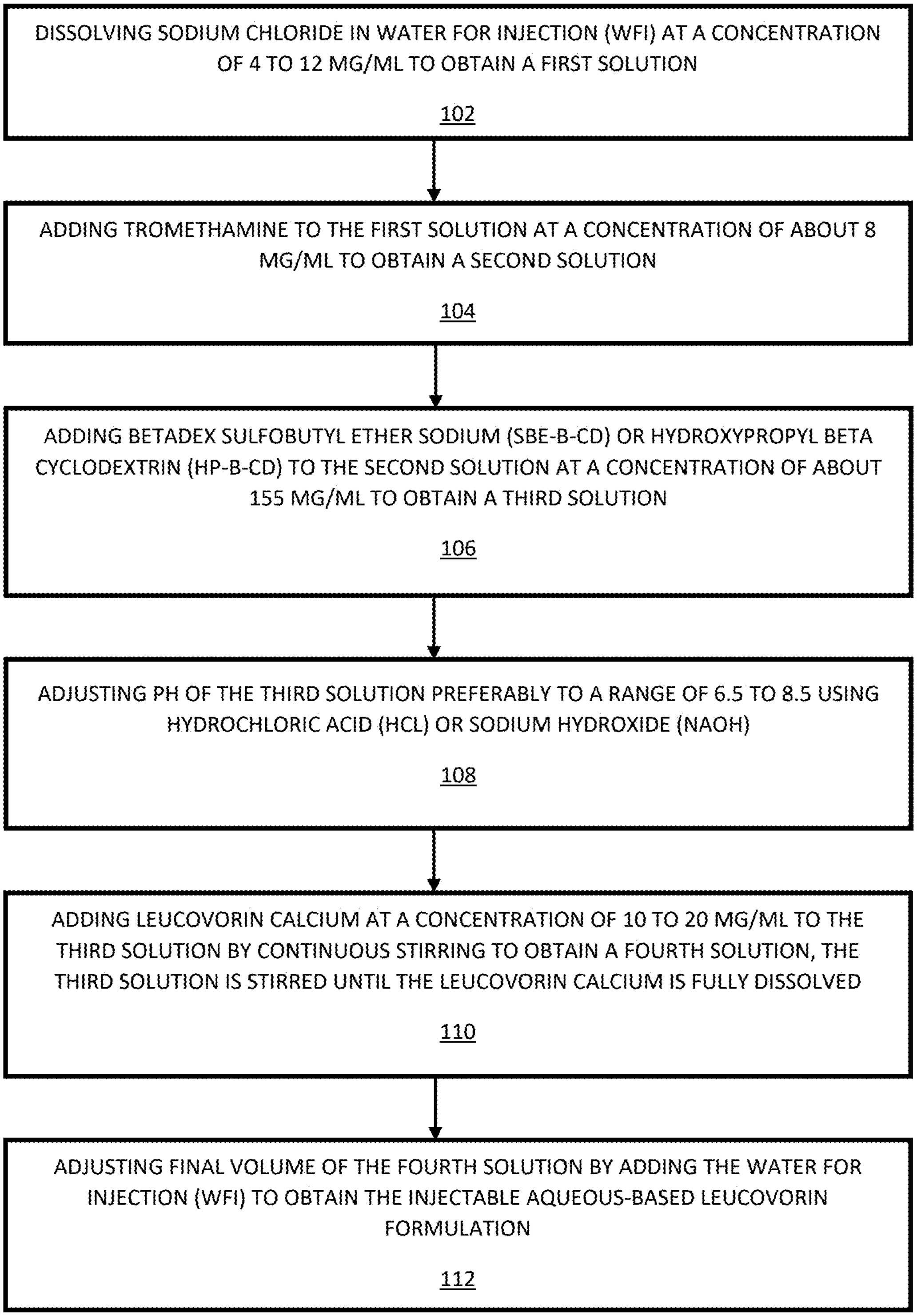
DISSOLVING SODIUM CHLORIDE IN WATER FOR INJECTION (WFI) AT A CONCENTRATION OF 4 TO 12 MG/ML TO OBTAIN A FIRST SOLUTION
102
ADDING TROMETHAMINE TO THE FIRST SOLUTION AT A CONCENTRATION OF ABOUT 8 MG/ML TO OBTAIN A SECOND SOLUTION
104
ADDING BETADEX SULFOBUTYL ETHER SODIUM (SBE-B-CD) OR HYDROXYPROPYL BETA CYCLODEXTRIN (HP-B-CD) TO THE SECOND SOLUTION AT A CONCENTRATION OF ABOUT 155 MG/ML TO OBTAIN A THIRD SOLUTION
106
ADJUSTING PH OF THE THIRD SOLUTION PREFERABLY TO A RANGE OF 6.5 TO 8.5 USING HYDROCHLORIC ACID (HCL) OR SODIUM HYDROXIDE (NAOH)
108
ADDING LEUCOVORIN CALCIUM AT A CONCENTRATION OF 10 TO 20 MG/ML TO THE THIRD SOLUTION BY CONTINUOUS STIRRING TO OBTAIN A FOURTH SOLUTION, THE THIRD SOLUTION IS STIRRED UNTIL THE LEUCOVORIN CALCIUM IS FULLY DISSOLVED
110
ADJUSTING FINAL VOLUME OF THE FOURTH SOLUTION BY ADDING THE WATER FOR INJECTION (WFI) TO OBTAIN THE INJECTABLE AQUEOUS-BASED LEUCOVORIN FORMULATION
112

INJECTABLE LEUCOVORIN FORMULATIONS AND METHODS OF PREPARING SAME

CROSS-REFERENCE TO RELATED APPLICATIONS

This application claims the benefit of priority from U.S. application Ser. No. 18/991,888 filed Dec. 23, 2024, the contents of which are hereby incorporated herein by reference in their entirety.

FIELD OF THE DISCLOSURE

The present disclosure relates to a stable, ready-to-use aqueous injectable pharmaceutical formulations comprising leucovorin or a pharmaceutically acceptable salt thereof, a solubilizer, a co-solubilizer, a buffering agent, a pH adjusting agent and a pharmaceutically acceptable vehicle. The disclosure further relates to processes for the preparation of such formulations and their use in the treatment of megaloblastic anemias due to folic acid deficiency, methotrexate toxicity, and/or in combination with 5-fluorouracil in the treatment of cancer.

BACKGROUND

Leucovorin, also known as folinic acid, is one of several active, chemically reduced derivatives of folic acid. It is widely used as an antidote to folic acid antagonists such as methotrexate and in combination with 5-fluorouracil (5-FU) in the treatment of various cancers, including metastatic colorectal cancer. Traditionally, leucovorin has been made available as a low-strength injectable solution (e.g., 3 mg/mL of leucovorin base), or as a lyophilized powder for injection in higher strengths (e.g., 50 mg, 100 mg, 200 mg, 350 mg or 500 mg leucovorin base per vial). The lyophilized forms require reconstitution with a suitable diluent, such as Bacteriostatic Water for Injection, USP, which contains benzyl alcohol or with Sterile Water for Injection, USP, prior to administration. However, this process is time-consuming, labour-intensive, and requires stringent aseptic handling, increasing the risk of error in dosing and contamination. Consequently, there has been growing demand for ready-to-use injectable formulations that eliminate the need for reconstitution.

Formulating such stable aqueous injections of leucovorin salt poses significant challenges due to the compound's low aqueous solubility and tendency to crystallize during storage. Crystallization results in the formation of particulate matter, which not only compromises the physical stability of the product but also poses serious risks to patient safety, especially when administered intravenously. Several strategies have been proposed to address these limitations.

For example, EP0416232 provides stabilized injectable compositions using additives such as benzyl alcohol, tromethamine, and monothioglycerol.

EP1640008 describes aqueous formulations of 5-formyl-(6S)-tetrahydrofolic acid with buffering agents and antioxidants such as ascorbic acid.

U.S. Pat. No. 4,931,441 presents an aqueous solution of leucovorin calcium at 6.35 mg/mL, but the low concentration limits therapeutic benefit and does not solve the precipitation problem.

Some commercial products, for example, those marketed by Bedford Laboratories, which were also recommended to be stored at 2-8° C., have been recalled from market due to discovery of visible crystalline particulate matter as documented by FDA MedWatch. This issue thus highlights that current approaches are inadequate in ensuring long-term physical stability. Therefore, despite these advancements, solubility-related stability issues remain a major concern, especially in liquid formulations of leucovorin calcium intended for long-term refrigerated storage.

EP0427078 reports complexes of leucovorin salts with cyclodextrins which are stable at acidic pH. To prepare the complexes, 3 methods are suggested, wherein the first one involves dissolving the folinic acid directly in an aqueous solution of the chosen cyclodextrin and the solution obtained is stirred preferably at ambient temperature; the complex is separated by cold precipitation, preferably at a temperature of between 0° C. and 5° C. The second method involves dissolving the folinic acid and the chosen cyclodextrin in a hot water/sodium hydroxide solution while stirring and separating the complex by lyophilization. The third method involves dissolving the calcium salt of folinic acid and the chosen cyclodextrin in hot water while stirring and separating the complex by lyophilization or by spray drying. The complexes are suitable for oral administration by the use of liquid oral formulations such as syrups or solid oral compositions such as tablets, sugar coated pills, soft or hard capsules or single dose sachets. However, there is no suggestion of formulating folinic acid salt and cyclodextrin complexes in stable injectable formulations that demonstrate long-term stability under refrigerated storage conditions.

Therefore, there remains a need for stable injectable formulations of leucovorin calcium. Certain embodiments of the present invention are designed to meet these and other ends.

SUMMARY

In some embodiments, the present invention provides injectable formulations comprising leucovorin calcium, a cyclodextrin derivative and other pharmaceutically acceptable excipients which are prepared by adding the leucovorin calcium salt, cyclodextrin derivative(s) and excipients in a specific sequence and maintaining the optimum pH of the formulation and supplying the formulation in suitable packaging configurations in glass vial.

Leucovorin calcium injection exhibits pH-dependent degradation, with its chemical stability being strongly influenced by the pH of the formulation. Deviation from the optimal pH range can accelerate degradation, leading to reduced potency and increased impurity formation. Thus, maintaining the pH within a carefully controlled range along with preventing the crystallization of active during the shelf life of formulation when stored at recommended temperature is critical for ensuring the physico-chemical integrity of the formulation over its shell life.

The inventors of the present invention have developed a practical solution to address the issue of crystallization throughout the shelf-life of the product, through extensive experimentation, resulting in a stable injectable aqueous formulation of leucovorin calcium. The inventors of present invention discovered that when cyclodextrin derivatives are used to make complexes with leucovorin calcium in a specific ratio and when the formulation is maintained within an optimal pH range with the use of additional excipients, the formulation maintains stability without formation of crystals under storage conditions.

The inventors of present invention developed stable, aqueous injectable pharmaceutical formulation of leucovorin calcium and cyclodextrin derivatives and other excipients suitable for injection formulations that remain stable during shelf life. These formulations, in addition to leucovorin calcium and cyclodextrin derivatives, further incorporate excipients such as co-solubilizers, buffering agents, pH adjusting agents and a pharmaceutically acceptable vehicle.

Furthermore, the present inventors also discovered that the sequence of addition of leucovorin calcium, cyclodextrin derivatives and other excipients during preparation of the formulation plays a critical role in preventing crystallization and ensuring both chemical and physical stability during storage and handling.

The present invention provides a stable, aqueous injectable formulation of leucovorin calcium. In some embodiments, the present invention relates to an injectable, ready-to-use composition comprising a therapeutically effective amount of leucovorin calcium, a solubilizer, a co-solubilizer, a buffering agent, a pH adjusting agent and a pharmaceutically acceptable vehicle.

In certain embodiments, the formulation comprises leucovorin calcium at a concentration of about 5 mg/mL to about 25 mg/mL, a cyclodextrin or its derivative as a solubilizer, a co-solubilizer, a buffering agent, and pharmaceutically acceptable vehicle. In other embodiments, the solubilizer is a cyclodextrin derivative at a concentration of about 1 mg/mL to about 300 mg/mL. In further embodiments, the co-solubilizer is sodium chloride, present at about 2 mg/mL to about 10 mg/mL, and the buffering agent is tromethamine, present at about 1 mg/mL to about 10 mg/mL. In some embodiments, the pH is adjusted by using a combination of hydrochloric acid and sodium hydroxide at a suitable amount. In other embodiments, water for injection is used as the pharmaceutically acceptable vehicle to make up the volume to 1 mL.

In some embodiments, the pH of the formulation is maintained in the range of about 6.5 to about 8.5, which contributes to the chemical stability of the pH-sensitive leucovorin salt. In other embodiments, the formulation remains physically and chemically stable when stored under refrigerated conditions (2° C. to 8° C.) over its intended shelf life.

In certain embodiments, no crystallization is observed during storage of the formulation of present invention, and the solution remains clear and free of particulate matter throughout the shelf life. This is achieved by the selection and concentration of excipients and by controlling the manufacturing process, including the order of ingredient addition and pH adjustment.

Another aspect of the invention relates to the manufacturing process, wherein the excipients are added in a specific sequence. Notably, the pH is adjusted to the desired range prior to the addition of leucovorin calcium, which minimizes the formation of degradation impurities and supports long-term stability.

In further embodiments, the formulation is free of preservatives and is intended for intravenous (IV) or intramuscular (IM) administration. Some embodiments of the present invention provide single-dose vials with fill volumes of 5 mL, 35 mL, or 50 mL, selected based on typical clinical dosing requirements to support ease of use in hospital and clinical settings.

In other embodiments, the formulation is suitable for the treatment of megaloblastic anemia due to folic acid deficiency when oral therapy is not feasible, methotrexate toxicity, and/or in combination with 5-fluorouracil in the treatment of cancer and as rescue after high dose methotrexate therapy in osteosarcoma.

Accordingly, embodiments of the present invention provide a practical, scalable, and regulatory-compliant solution to the longstanding challenges of stability and solubility in leucovorin calcium injectable formulations. Certain embodiments also improve clinical efficiency and patient safety by eliminating the need for reconstitution prior to administration, while enhancing hospital compliance through reduced drug wastage.

BRIEF DESCRIPTION OF THE DRAWINGS

A clear understanding of the key features of the invention summarized above may be had by reference to the appended drawings, which illustrate the method and system of the invention, although it will be understood that such drawings depict preferred embodiments of the invention and, therefore, are not to be considered as limiting its scope with regard to other embodiments which the invention is capable of contemplating. Accordingly:

FIG. 1 depicts a method for preparing an injectable aqueous-based leucovorin formulation according to various embodiments of the present invention.

Like reference numerals refer to like parts throughout the several views of the drawings.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion.

Nevertheless, the specification and claims should be read with the understanding that such combinations are entirely within the scope of the invention and the claims. An injectable aqueous-based leucovorin formulation and preparation method thereof is discussed herein. In the following description, for purposes of explanation, numerous specific details are set forth in order to provide a thorough understanding of the present invention. It will be evident, however, to one skilled in the art that the present invention may be practiced without these specific details. The present disclosure is to be considered as an exemplification of the invention and is not intended to limit the invention to the specific embodiments illustrated by the FIGURES or description below. The present invention will now be described by referencing the appended FIGURES representing preferred embodiments.

Leucovorin, also known as folinic acid, Citrovorum factor, or 5-formyl-5,6,7,8-tetrahydrofolic acid, has the chemical name Calcium N-[p-[[[(6RS)-2-amino-5-formyl-5,6,7,8-tetrahydro-4-hydroxy-6-pteridinyl]methyl]amino]benzoyl]-L-glutamate (1:1). The structural formula of leucovorin calcium is:

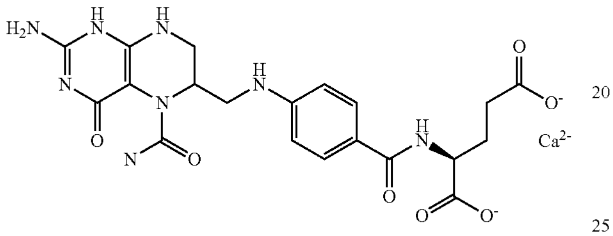

Leucovorin calcium is a white to light yellow crystalline powder with the molecular formula: $C_{20}H_{21}NO_7Ca \cdot H_2O$ and a molecular weight of 511.50.

As used herein, the term "leucovorin calcium" is intended to encompass leucovorin per se, as well as its pharmaceutically acceptable derivatives. Such derivatives include, but are not limited to, pharmaceutically acceptable salts (including the calcium salt and sodium salt), hydrates, solvates, anhydrates, stereoisomers (including diastereomers and enantiomers), racemates, tautomers and polymorphs.

In some embodiments, the present invention provides a stable, ready-to-use pharmaceutical formulation comprising leucovorin calcium or its pharmaceutically acceptable solvate, hydrate, or mixture thereof. Preferably, the leucovorin is present as the calcium salt in the formulation of present invention.

In some embodiments, the invention relates to the development of physically and chemically stable injectable formulations comprising leucovorin calcium wherein the concentration of leucovorin calcium in the formulation ranges from about 5 mg/mL to about 25 mg/mL of total formulation, preferably about 10 mg/mL of total formulation.

Leucovorin calcium is a chemically and physically labile compound, known for its sensitivity to light, oxidation, hydrolysis, and pH-dependent degradation, which can lead to the formation of impurities over time. In aqueous media, it exhibits limited solubility and is prone to crystallization, particularly under refrigerated storage conditions (2° C. to 8° C.). The phenomenon of crystallization is driven by reduced solubility at lower temperatures and the presence of supersaturation of active compound in injectable aqueous formulations. Leucovorin calcium injection formulations have historically faced crystallization challenges, resulting in multiple product recalls. Given its susceptibility to crystallization, ensuring the physical stability of leucovorin calcium through effective crystal suppression is a key aspect of formulation design. This highlighted the need for a formulation strategy that ensures solubility, physical stability, and visual clarity throughout the shelf life.

The inventors of the present invention conducted an in-depth solubility assessment and identified cyclodextrin-based solubilizers as effective agents for enhancing aqueous solubility and inhibiting crystal formation. These substituted cyclodextrins form inclusion complexes with leucovorin calcium, reducing intramolecular interactions that can trigger nucleation and precipitation. The resulting formulations, containing leucovorin calcium at a therapeutically effective concentration preferably about 10 mg/mL, remain clear and physically stable under refrigeration without requiring reconstitution.

In some embodiments, the formulations of present invention are water-based formulations. Therefore, water soluble cyclodextrin derivatives are preferred as solubilizers in the formulations of present invention. In some embodiments, the water-soluble cyclodextrin derivatives used as solubilizers in the formulation of present invention are selected from, but not limited to, the group consisting of: Sulfobutyl Ether β-Cyclodextrin (SBE-β-CD), Hydroxypropyl β-Cyclodextrin (HP-β-CD), Hydroxypropyl γ-Cyclodextrin (HP-γ-CD), Methyl β-Cyclodextrin (M-β-CD), Carboxymethyl β-Cyclodextrin, Glucosyl β-Cyclodextrin, randomly Methylated β-Cyclodextrin (RM-β-CD), and their pharmaceutically acceptable salts; and a combination of two or more thereof.

β-Cyclodextrin, also known as Betadex, is a heptasaccharide composed of seven α-(1→4)-linked D-glucopyranosyl units forming a cyclic structure. It is a pharmacologically inactive excipient. Betadex Sulfobutyl Ether Sodium is synthesized by the alkylation of Betadex with 1,4-butane sulfone under basic conditions. The average degree of substitution of SBE-β-CD is NLT 6.2 and NMT 6.9, and it has a molecular formula as $C_{42}H_{70}\text{-}nO_{35}(C_4H_8SO_3Na)n$ (n=6.2 to 6.9) and a molecular weight of 2163 g/mol (n=6.5). The structure is represented below:

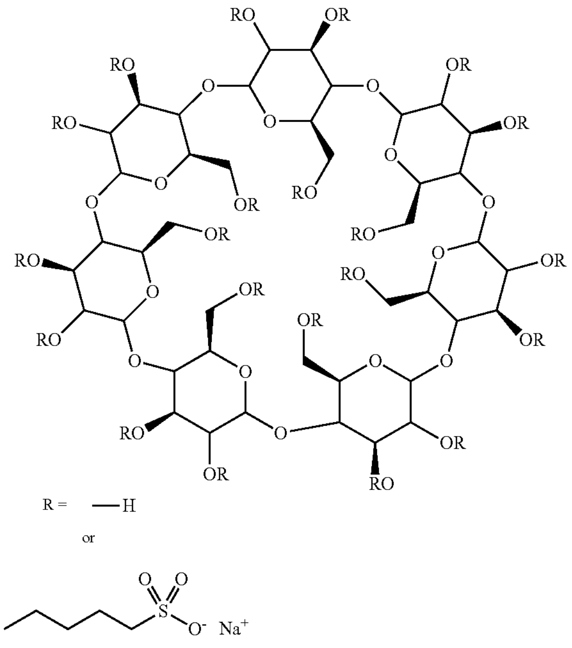

Complexation with cyclodextrins not only enhances the aqueous solubility of leucovorin calcium but also contributes to improved formulation stability by shielding labile functional groups from degradation and minimizing the risk of crystallization during storage. The resulting molecule forms inclusion complexes with suitable guest molecules, including leucovorin calcium, thereby acting as a solubilizing and stabilizing agent.

In various embodiments of the present invention, a critical factor in achieving a physically and chemically stable, clear, ready-to-use injectable formulation of leucovorin calcium lies in the careful selection and optimization of the cyclodextrin derivative used as a solubilizing agent. Accordingly, the inventors systematically evaluated multiple cyclodextrin derivatives across three fundamental experimental parameters, which together form the scientific foundation for the inventive step: saturation solubility, binding constant, and freeze-thaw resistance.

In some embodiments, the inventors conducted a saturation solubility study to determine the ability of various cyclodextrin derivatives to enhance the solubility of leucovorin calcium under physiologically and pharmaceutically relevant conditions. Leucovorin was added to aqueous systems containing cyclodextrin at different concentrations, both with and without any other excipient, and the mixture was incubated at −20° C. and 2-8° C. to simulate storage and use conditions. The solutions were shaken for 24 hours and then filtered to remove undissolved material before assay. A significant difference in saturation solubility was observed depending on the type and concentration of cyclodextrin by maintaining clear solutions even at low temperatures. This experimental approach confirmed that these specific cyclodextrins effectively maintain leucovorin in solution within the desired concentration range (e.g., 10 mg/mL), thereby suppressing the onset of nucleation and crystal growth during storage.

In other embodiments, the inventors further investigated the binding affinity between leucovorin calcium and the cyclodextrin derivatives by calculating the binding constant (K), which indicates the strength and extent of complex formation. A moderate binding constant is desirable, strong enough to stabilize the drug in solution but not so high as to sequester the drug and alter its pharmacokinetics or bioavailability. The study also indicated that if a binder is too weak, then it may fail to inhibit crystallization, while if too strong, a binder may compromise drug release and therapeutic efficacy, therefore a balance is required that the selected cyclodextrins uniquely achieve.

In further embodiments, the physical robustness of the cyclodextrin-stabilized formulations was tested under thermal stress conditions to evaluate their real-world storage stability. Freeze-thaw studies involved cycling the formulations between −20° C. (48 hours) and 25° C. (48 hours) for three repetitions.

In some embodiments, the cyclodextrin derivative is selected from Sulfobutyl Ether β-Cyclodextrin (SBE-β-CD), Hydroxypropyl β-Cyclodextrin (HP-β-CD), Hydroxypropyl γ-Cyclodextrin (HP-γ-CD), Methyl β-Cyclodextrin (M-β-CD), Carboxymethyl β-Cyclodextrin, Glucosyl β-Cyclodextrin, and randomly methylated β-Cyclodextrin (RM-β-CD), and their pharmaceutically acceptable salts or combinations thereof.

In other embodiments, the inventors of present invention surprisingly found that the cyclodextrin derivative such as SBE-β-CD, HP-β-CD showed optimal performance across all evaluation parameters. In certain embodiments, the cyclodextrin derivatives used in the formulations of the present invention as a solubilizer are SBE-β-CD, HP-β-CD or a combination thereof.

In some embodiments, for SBE-β-CD, the calculated binding constant was approximately 43.1 $M^{-1}$, suggesting a 1:1 stoichiometry with leucovorin and indicating a low but adequate complexation profile. Notably, this value is well below the critical threshold of $1\times10^5$ $M^{-1}$, beyond which significant systemic interactions could be anticipated. Therefore, SBE-β-CD forms a reversible inclusion complex with leucovorin that enhances solubility while preserving the molecule's pharmacological activity and disposition profile. In other embodiments, the formulations of present invention comprising SBE-β-CD or HP-β-CD maintain optical clarity and solution stability throughout all tested cycles preferably form about 20 cycles, about 18 cycles, about 16 cycles, about 14 cycles, about 12 cycles and about 10 cycles at refrigerated temperatures. In some embodiments, the complexes prepared in the present invention comprising leucovorin calcium and SBE-β-CD remain stable up to at least 10 cycles. The data conclusively demonstrated that the selected cyclodextrins effectively suppress both cooling-induced precipitation and recrystallization during thawing, which are primary concerns in the commercial viability of injectable products.

In various embodiments of the present invention, the amount of cyclodextrin derivative incorporated into the formulation is carefully optimized to strike a balance between drug solubilization, physical and chemical stability, and clinical safety. In some embodiments, the concentration of cyclodextrin derivative in the formulation may range from about 1 mg/mL to about 300 mg/mL, from about 5 mg/mL to about 250 mg/mL, from about 10 mg/mL to about 200 mg/mL, from about 15 mg/mL to about 150 mg/mL, from about 20 mg/mL to about 100 mg/mL, more preferably from about 40 mg/mL to about 80 mg/mL, and most preferably about 50 mg/mL.

In some embodiments, during the studies it was found that very low amount of the cyclodextrin derivative is insufficient to form a stable and effective inclusion complex with leucovorin calcium, particularly at drug loading of 10 mg/mL. Inadequate complexation at these levels increases the risk of supersaturation and crystallization, especially under refrigerated conditions (2° C. to 8° C.), leading to visible particulates, compromised injectability, and product recall liabilities.

On the other hand, very high concentrations of cyclodextrins pose potential safety concerns. High doses of intravenously administered cyclodextrins have been associated with renal accumulation and nephrotoxicity, particularly in vulnerable patient populations such as those with impaired kidney function or undergoing chemotherapy. Moreover, excess cyclodextrin in the formulation may result in viscosity and osmolality related issues, potentially affecting injectability and patient comfort.

Therefore, in some embodiments, the concentration of about 10 mg/mL to about 100 mg/mL of cyclodextrin derivative selected from SBE-β-CD or HP-β-CD has been surprisingly identified through extensive experimental screening as the optimal level that ensures complete solubilization of leucovorin calcium at target concentrations (e.g., 10 mg/mL), suppression of crystallization during long-term storage, including after freeze-thaw cycles, binding constant sufficiently low to avoid significant impact on pharmacokinetics, and a favorable clinical safety profile in systemic administration.

Without being bound to any theory, it has been known that leucovorin calcium salt, when introduced into an aqueous environment, undergoes dissociation to yield the leucovorin base, which is the actual species that participates in complexation with the cyclodextrin derivative. As a result, the interaction between leucovorin and the cyclodextrin is mechanistically governed by the base form rather than the salt. This complexation process is influenced by the dissociation constant of leucovorin calcium, which thereby serves as a key parameter in optimizing the relative amounts of leucovorin calcium salt and cyclodextrin derivative. The present inventors, by carefully regulating this balance and determining the ratio of leucovorin calcium with cyclodextrin derivative, have developed a formulation that ensures effective complex formation without excessive sequestration of the active drug, leading to improved aqueous solubility, preservation of pharmacological activity, and enhanced physical and chemical stability throughout the product's shelf life.

In some embodiments, the formulation includes leucovorin and a water-soluble cyclodextrin derivative in a weight ratio ranging from about 1:1 to about 1:30. In certain embodiments, the ratio may be selected from about 1:2 to about 1:28, preferably from about 1:2.5 to about 1:25, preferably from about 1:3 to about 1:20, preferably from about 1:3.5 to about 1:15, preferably from about 1:4 to about 1:10.

In other embodiments, a weight ratio of leucovorin to cyclodextrin derivative of about 1:5 is used. This ratio was observed to maintain solution clarity and suppress precipitation over extended storage at 2° C. to 8° C. It supports the formation of an inclusion complex that improves the solubility of leucovorin calcium while keeping the amount of cyclodextrin within pharmaceutically acceptable limits.

In some embodiments, the ratios below 1:1 may not adequately stabilize the solution and may lead to visible precipitation during shelf life. Conversely, ratios above 1:30, although capable of further improving solubility, may result in unnecessarily high cyclodextrin content. Elevated levels of cyclodextrins such as SBE-β-CD or HP-β-CD may raise safety concerns in certain patient populations, particularly those with renal impairment; and might also have osmolality challenges as the formulation is administered by either intravenous or intramuscular route.

In some embodiments, the formulations of the present invention further comprise one or more co-solubilizers in addition to cyclodextrin derivatives to further enhance the aqueous solubility and physical stability of leucovorin calcium. In certain embodiments, the co-solubilizer serves a supplementary role in modifying the ionic strength, maintaining isotonicity, and assisting in suppression of crystallization by influencing solute-solvent interactions. Suitable co-solubilizers include, but are not limited to, pharmaceutically acceptable electrolytes, amino acids, polyols, and neutral salt such as electrolytes and neutral salt selected from sodium chloride, potassium chloride, magnesium sulfate, sodium gluconate, sodium thiosulfate, sugar salts, and sodium cholate selected from amino acids and derivatives: arginine, arginine hydrochloride, glycine, glutamine, glutamic acid, asparagine, aspartic acid, alanine, valine, tyrosine, tryptophan, threonine, serine, proline, phenylalanine, methionine, lysine, leucine, isoleucine, histidine, and histidine hydrochloride; polyols and sugar alcohols selected from sorbitol, mannitol, glycerin, propylene glycol; other co-solubilizers selected from polyethylene glycol, poloxamer, lactic acid, citric acid and its salts, tartaric acid, and sucrose or other saccharides.

In further embodiments, sodium chloride is employed as the co-solubilizer. Sodium chloride contributes to the ionic environment of the formulation and influence the solubility profile of weakly ionizable compounds like leucovorin calcium. It aids in achieving a final formulation osmolality in the range of about 280 to 600 mOsm, preferably at about less than 400 mOsm which is physiologically acceptable for parenteral administration.

In various embodiments, the concentration of the co-solubilizer may broadly range from about 2 mg/mL to about 12 mg/mL, preferably from about 3 mg/mL to about 8 mg/mL, and most preferably about 4-5 mg/mL. In some embodiments, the co-solubilizer comprises sodium chloride at a concentration of about 5 mg/mL, contributing to an optimal formulation profile that is clear, stable, isotonic, and suitable for direct intravenous or intramuscular administration without the need for reconstitution or dilution.

In other embodiments, the present invention provides formulations further comprising one or more buffering agents to maintain the pH of the injectable composition within a physiologically acceptable and chemically stable range throughout the shelf life.

As used herein, the term "buffering agent" refers to an ingredient or combination of ingredients that maintains pH stability (i.e., pH within a desired range) during shelf life.

Leucovorin calcium is highly sensitive to pH, and even slight deviations from the optimal pH range can accelerate the formation of degradation impurities. Therefore, maintaining the formulation pH within a narrow, controlled range of about 6.5 to about 8.5, more preferably about 7.5 to 8.5 and most preferably about 8.0 to about 8.5, is critical for preserving the chemical integrity of the active ingredient during manufacturing and throughout the shelf life. In some embodiments, the buffering agent is selected from pharmaceutically acceptable organic or inorganic acid-base pairs that are compatible with leucovorin calcium and do not adversely affect its chemical stability or solubility. Suitable buffering agents include, but are not limited to, tromethamine (Tris), phosphate buffers, acetate buffers, citrate buffers, and other biologically compatible Good's buffers such as TAPS, AMPSO, TABS, AMPD, Gly-Gly, HEPBS, Bicinc, Tricine, EPPS (HEPPS), TES, POPSO, HEPPSO, TAPSO, MOBS, DIPSO, HEPES, PIPES, MOPSO, MOPS, BES, Bis-Tris Propane, and ACES, or combinations thereof. In a preferred embodiment, tromethamine is used as the buffering agent to maintain the formulation pH in the range of about 6.5 to about 8.5, more preferably about 7.5 to 8.5 and most preferably about 8.0 to about 8.5. Tromethamine, a weak base, effectively buffers the solution in the slightly alkaline pH range, which is particularly beneficial for preserving the chemical stability of leucovorin calcium over long-term refrigerated storage.

The concentration of the buffering agent may range from about 1 mg/mL to about 10 mg/mL, and in a preferred embodiment, tromethamine is present at a concentration of about 7 mg/mL in the final formulation. The buffering agent plays a pivotal role in maintaining the desired pH throughout manufacturing, storage, and administration, thereby preventing pH-related degradation pathways that are known to impact leucovorin stability.

In some embodiments, the formulations of the present invention are optimized by carefully selecting the weight ratios between leucovorin, a cyclodextrin derivative, and a buffering agent to achieve desirable solubility, clarity, and pH stability. In some embodiments, the weight ratio of leucovorin to cyclodextrin derivative to tromethamine is in the range of about about 1:2:0.2, about 1:3:0.3, about 1:4:0.4, about 1:4:0.5, about 1:5:0.5, about 1:5:0.6, about 1:5:0.7, about 1:6:0.7, about 1:6:0.8, about 1:7:0.8, about 1:7:1.0, about 1:8:1.0, about 1:10:1.0, about 1:12:1.2, and about 1:15:1.5. In other embodiments, the ratio is about 1:5:0.7, which has been demonstrated to maintain physicochemical stability during refrigerated storage and under accelerated conditions.

In some embodiments, the formulations of the present invention further comprise one or more pH adjusting agents to maintain the pH of the solution within a range suitable for ensuring chemical stability and minimizing degradation of leucovorin calcium.

As used herein, the terms "pH adjusting agent" or "pH adjuster" refer to an ingredient or combination of ingredients that is used during manufacturing to achieve a target pH.

To achieve and maintain the desired pH, in some embodiments, the formulations include pH adjusting agents selected from pharmaceutically acceptable acids and bases. In particular embodiments, the acid and base used for pH adjustment are hydrochloric acid (HCl) or sodium hydroxide (NaOH), or a combination thereof.

In certain embodiments, the formulations of the present invention further comprise a pharmaceutically acceptable vehicle. In some embodiments, the pharmaceutically acceptable vehicle is water for injection.

In one or more embodiments, the formulation of the present invention exhibits physical and chemical stability under long-term and accelerated storage conditions. Leucovorin calcium, being a chemically and physically labile compound, is particularly susceptible to pH-dependent degradation, hydrolysis, and crystallization, especially under refrigerated conditions (2° C. to 8° C.). The optimized formulation comprising leucovorin calcium, cyclodextrin derivatives, co-solubilizers, buffering agents, and pH adjusters has been specifically designed to overcome these limitations.

As used herein, the physical and chemical stability of the formulation of the present invention is defined by the absence of crystallization and the controlled level of degradation impurities. Specifically, the formulation maintains Impurity A (4-Amino Benzoyl Glutamic Acid) at levels not more than 2.0% by weight of leucovorin calcium, Impurity F (10-Formyl Dihydrofolic Acid) at levels not more than 1.0% by weight of leucovorin calcium, any unspecified impurity at levels not more than 0.5%, and total impurities at levels not more than 2.5% by weight of leucovorin calcium, as determined by high-performance liquid chromatography (HPLC).

In one embodiment, the formulation remains stable for an extended period, such as at least 6 months, preferably at least about 9 months, more preferably at least about 18 months, and most preferably for at least about 24 months when stored under refrigerated conditions at a temperature of about 2° C. to about 8° C., and protected from light.

In other embodiments, the formulation also remains physically and chemically stable for up to 3 months when stored at an accelerated temperature of about 25° C.±2° C. and 60%±5% RH, when protected from light.

In further embodiments, the formulations withstand temperature excursions and multiple freeze-thaw cycles without loss of clarity or onset of crystallization, further confirming its robustness and suitability for commercial use.

According to some embodiments, the formulations of the present invention are free from preservatives. According to other embodiments, the formulations of the present invention do not comprise antioxidants.

In some embodiments, the present invention provides an optimized, clear, ready-to-use, stable aqueous injectable formulation comprising leucovorin calcium at a concentration of about 10 mg/mL, a water-soluble cyclodextrin derivative such as sulfobutyl ether β-cyclodextrin (SBE-β-CD) or hydroxypropyl β-cyclodextrin (HP-β-CD) at a concentration of about 50 mg/mL, a co-solubilizer such as sodium chloride at a concentration of about 5 mg/mL, a buffering agent such as tromethamine at a concentration sufficient to maintain a pH between about 8.0 and about 8.5, a pH adjuster (e.g., hydrochloric acid and/or sodium hydroxide), and water for injection as the vehicle. In some embodiments, these formulations are free from preservatives and antioxidants and are aseptically filled into amber glass vials under a nitrogen atmosphere to minimize oxidative degradation and light-induced instability.

Some embodiments of the present invention provide a process for preparing a clear, ready-to-use, stable aqueous injectable formulation comprising leucovorin calcium and a water-soluble cyclodextrin derivative. In some embodiments, the process begins by charging approximately 90% of the total batch volume of water for injection into a clean compounding vessel maintained at about 20° C. to 25° C. In other embodiments, filtered nitrogen gas is purged into the water until the dissolved oxygen (DO) level drops below 2 ppm, thereby minimizing oxidative degradation of leucovorin calcium. In some embodiments, a pre-measured quantity of a co-solubilizer, such as sodium chloride, is added under continuous stirring until a clear solution is obtained. In some embodiments, this is followed by the sequential addition of a buffering agent, such as tromethamine, and a cyclodextrin derivative (e.g., SBE-β-CD or HP-β-CD), each added with adequate stirring to ensure complete dissolution.

In some embodiments, the initial pH of the resulting solution is measured and adjusted to the desired range of about 6.5 to about 8.5, preferably between about 8.0 and 8.5, using a pH adjusting agent such as hydrochloric acid and/or sodium hydroxide. In certain embodiments, leucovorin calcium is then added under continuous stirring until fully dissolved, forming a stable inclusion complex with the cyclodextrin derivative. In some embodiments, the pH is checked again and readjusted, if necessary, to fall within the defined specification. In other embodiments, the batch volume is brought up to 100% with water for injection, and the final pH is confirmed. In further embodiments, the bulk solution is then filtered through a 0.22 µm sterile membrane filter and aseptically filled into amber glass vials under a nitrogen blanket to preserve the formulation's integrity. In some embodiments, the filled vials are then stoppered, sealed, labelled, and packaged as single-dose containers in suitable fill volumes (for example, 5 mL, 35 mL, or 50 mL), completing the manufacturing process.

According to some embodiments, it has been demonstrated that when leucovorin calcium has been added to the pH adjusted solution of co-solubilizer, buffer and cyclodextrin derivative then a stable and clear solution is consistently achieved. In some embodiments, this order of addition facilitates the establishment of a well-buffered medium that optimally supports the complexation of leucovorin calcium upon its introduction, without inducing premature precipitation or pH imbalance.

FIG. 1 illustrates a method for preparing an injectable aqueous-based leucovorin formulation according to various embodiments of the present invention. At step 102, the method includes dissolving sodium chloride at a concentration of 4 to 12 mg/mL in Water for Injection (WFI) to obtain a first solution. At step 104, the method includes adding tromethamine at a concentration of 8 mg/mL to the first solution to obtain a second solution. At step 106, the method includes adding Betadex Sulfobutyl Ether Sodium (SBE-β-CD) or Hydroxypropyl Beta Cyclodextrin (HP-β-CD) to the second solution up to 65 mg/mL to obtain a third solution. At step 108, the method includes adjusting pH of the third solution to a range of 6.5 to 8.5 using hydrochloric acid (HCl) and/or sodium hydroxide (NaOH). At step 110, the method includes adding leucovorin calcium at a concentration of 10 to 20 mg/mL to the third solution by continuous stirring to obtain a fourth solution, the third solution is stirred until the Leucovorin calcium is fully dissolved. At step 112, the method includes adjusting the final volume of the fourth solution by adding the water for injection (WFI) to achieve a total volume of 1 mL and sterile filtered to obtain the injectable aqueous-based leucovorin formulation.

In an embodiment, the WFI is collected and maintained at a controlled temperature between 20° C. and 25° C. throughout the process to ensure the stability and solubility of leucovorin in the aqueous solution. After the collection of WFI, the next step involves purging the solution with filtered nitrogen gas. This reduces and controls the dissolved oxygen content in the aqueous solution, preventing oxidation and degradation of leucovorin. Nitrogen is introduced until the target dissolved oxygen content is achieved, ensuring the dissolved oxygen level falls within a predefined range that is optimal for the stability of the leucovorin formulation. At the last step, the final solution is sterile filtered and then filled in the glass vial followed by storage in 2-8° C. in order to ensure that the impurities are controlled.

Therefore, in some embodiments, the formulation process includes adding the co-solubilizer first to deoxygenated water, followed by the buffering agent, then the cyclodextrin derivative, with subsequent pH adjustment prior to introducing leucovorin calcium. In certain embodiments, this sequence ensures an environment conducive to the stable inclusion of the leucovorin calcium within the cyclodextrin cavity, preserves product clarity, and prevents crystallization, particularly under refrigerated conditions.

In some embodiments, the clear, ready-to-use aqueous injectable formulation of the present invention is filled into amber-colored Type I USP tubular glass vials. In some embodiments, the vials are sealed with pharmaceutical-grade rubber stoppers, optionally coated to minimize leachable or interaction with the drug product and further secured with aluminium flip-off seals. In other embodiments, the filling process is conducted under filtered nitrogen purging, which serves to displace dissolved and headspace oxygen such that headspace oxygen level is maintained below 2 ppm, thereby minimizing the potential for oxidation-related degradation over time.

In some embodiments, the inclusion of water-soluble cyclodextrin derivatives, such as SBE-β-CD and HP-β-CD, significantly improves the aqueous solubility of leucovorin calcium by forming reversible inclusion complexes, thereby reducing the risk of crystallization and precipitation during storage. Additionally, maintaining the pH in the range of about 8.0 to 8.5 using an appropriate buffering system further stabilizes the active ingredient by minimizing the formation of degradation products such as Impurity A and Impurity F and total impurities. In some embodiments, the total impurities are total degradation impurities. In some embodiments, the use of nitrogen purging during manufacturing and aseptic filling into amber glass vials further protects the formulation from oxidative degradation and light-induced instability.

In some embodiments, the injectable formulations of the present invention are filled into single-dose vials in convenient fill volumes such as 5 mL, 35 mL, and 50 mL, aligned with therapeutic dosing and institutional requirements. In certain embodiments, these packaging configurations reduce drug wastage and improve handling efficiency in hospital and clinical settings.

In some embodiments, the formulations of the present invention are filled/supplied in prefilled syringes.

In some embodiments, the formulations of the present invention demonstrate excellent robustness under stress conditions, including freeze-thaw cycles (e.g., 10 cycles of −20° C. for 24 hours followed by thawing at 2-8° C. for 24 hours), with no visible precipitation or loss of clarity.

In some embodiments, the clear, stable, ready-to-use aqueous formulations of the present invention are suitable for direct intravenous (IV) and intramuscular (IM) administration to a patient in need thereof. In certain embodiments, the formulations have been specifically optimized to be isotonic, pH-adjusted, and free from particulate matter, making it well-tolerated upon parenteral administration without the need for dilution or reconstitution prior to use. The absence of crystallization, along with its physical and chemical stability under refrigerated storage, ensures that the formulation retains therapeutic potency, safety, and clarity throughout its shelf life. Furthermore, the formulation's compatibility with intravenous and intramuscular administration routes offers flexibility in clinical settings, especially in oncology, emergency medicine, and rescue therapy for methotrexate toxicity or folate deficiency, where rapid and reliable delivery of leucovorin is critical.

In other embodiments, the present invention provides a method of treating a medical condition responsive to folinic acid therapy, comprising administering to a subject in need thereof an effective amount of the clear, ready-to-use aqueous injectable formulation comprising leucovorin calcium and a water-soluble cyclodextrin derivative as described herein. In some embodiments, the formulation of present invention is administered to a patient in need thereof suffering from conditions of methotrexate toxicity, folinic acid deficiency, and colorectal cancer in combination with 5-fluorouracil. In some embodiments, the formulation may be administered via intravenous (IV) or intramuscular (IM) injection, depending on clinical requirements.

In some embodiments, the stable, ready-to-use aqueous injectable pharmaceutical formulations of the present invention comprise leucovorin calcium provided in amber glass vials suitable for single-dose administration. In certain embodiments, the formulations of the present invention may be filled in various fill volumes to accommodate different dosing needs, with preferred packaging configurations selected from, but not limited to 5 mL, 10 mL, 15 mL, 20 mL, 25 mL, 30 mL, 35 mL, 40 mL, 45 mL and 50 mL vial sizes. In some embodiments, the formulations of present invention are provided in vial sizes of 5 mL, 35 mL and 50 mL.

The following examples are for the purpose of illustration of the invention only and are not intended to limit the scope of the present invention in any manner whatsoever.

EXAMPLES

Example 1

Table 1 (below) describes an exemplary formulation leucovorin calcium ready-to-use injection.

TABLE 1

| Sr No | Ingredients | Quantity-mg/mL |
|---|---|---|
| 1. | Leucovorin Calcium USP | Eq to 10.0 Leucovorin base |
| 2. | Sodium chloride USP | 4.0 |
| 3. | Tromethamine USP | 7.0 |
| 4. | Sulfobutyl ether β cyclodextrin | 50.0 |
| 5. | Hydrochloric Acid NF | q.s. to pH adj. |
| 6. | Sodium hydroxide NF | q.s. to pH adj. |
| 7. | Water for Injection USP | q.s. to 1.0 mL |
| 8. | Nitrogen NF¥ | As required |

The formulation described in Table 1 (above) can be prepared by the following steps:

1) Collected approximately 90% of water for injection (WFI) in primary compounding vessel, at 20-25° C.
2) Purged the filtered nitrogen into WFI. Stopped the nitrogen purging once the dissolved oxygen levels of <2 PPM is attained.
3) Added dispensed quantity of sodium chloride under continuous stirring until clear solution was observed.
4) Added dispensed quantity of Tromethamine under continuous stirring until clear solution observed.
5) Added dispensed quantity of Betadex Sulfobutyl Ether Sodium under continuous stirring to get clear solution.
6) Checked for the initial pH of the solution followed by adjusting pH between 6.5 to 8.5 (target: 8.0±0.2) using 3N HCL/IN NaOH solution.
7) Added dispensed quantity of Leucovorin API under continuous stirring.
8) Transferred the rinse solution to the compounding vessel under mixing. Stirred until clear solution is obtained with continuous filtered nitrogen flushing.
9) Checked the pH of solution and adjusted the pH to between 6.5 to 8.5 (target: 8.0±0.2) using 3N HCL/1 N NaOH.
10) Made up the volume of the solution to 100% of batch size using WFI Check final pH of solution (pH value 6.5-8.5) (pH limit: 8±0.2)
11) Used nitrogen during sterile filtration and aseptic filling to maintain head space oxygen with Nitrogen.
12) After flushing, filling was continued followed by stoppering sealing and then labelling, followed by packaging.

Example 2

Stability studies of formulation samples prepared by the process described in Example 1 were carried out to assess physical and chemical parameters, the details of which are tabulated below. Particulate matter study was carried out for samples incubated in an inverted orientation.

TABLE 2

| Stability Test Results | | | | | | |
|---|---|---|---|---|---|---|
| Test parameters | Acceptance | | 2-8° C. | | 25° C. ± 2° C. | |
| description | criteria | Initial | 3 month | 6 month | 3 month | 6 month |
| Description | A clear, colorless to yellow color solution, | Clear colorless solution | Clear colorless solution | Light pale-yellow Color solution | Pale yellow Color solution | Dark yellow Color solution |
| pH | 6.5-8.5 | 8.26 | 8.11 | 8.12 | 8.17 | 8.08 |
| Osmolality | NMT 600 | 384 | 385 | 384 | 383 | 383 |
| Assay | 90-120% | 104.9 | 104.2 | 103.7 | 102.2 | 100.6 |
| Related substance | | | | | | |
| Impurity A | NMT 2.0% | 0.065 | 0.211 | 0.421 | 0.711 | 1.392 |
| Impurity F | NMT 1.0% | 0.032 | 0.063 | 0.063 | 0.43 | 1.24 |
| Any unspecified impurity | NMT 0.5% | 0.038 | 0.055 | 0.104 | 0.107 | 0.173 |
| Total impurities | NMT 2.5% | 0.266 | 0.603 | 0.976 | 1.657 | 3.837 |

ND: Not Detected; NMT: Not more than

Conclusion: Based on the data described above in Table 2, it is evident that the formulation of present invention is stable over extended period with no crystallization as particulate matter was well within the specified norms along with chemical stability at 2-8° C. The formulation also withstood accelerated conditions of 25° C. for 3 months which helps the drug product to remain stable in case of short-term temperature excursions.

Example 3

A saturation solubility study was conducted at 2-8° C. and the results are depicted in below in Table 3.

TABLE 3

| Conc. of excipient | Assay (mg/mL) at 2-8° C. | Osmolality (mOsm/kg) |
|---|---|---|
| Leucovorin calcium (10 mg/mL), SBE-β-CD (100 mg/mL) | 18.48 | 344 |
| Leucovorin calcium (10 mg/mL), SBE-β-CD (100 mg/mL) Sodium Chloride (4 mg/mL) | 19.2 | 456 |
| Leucovorin calcium (10 mg/mL), SBE-β-CD (50 mg/mL) | 12.62 | NA |
| Leucovorin calcium (10 mg/mL), SBE-β-CD (50 mg/mL), Sodium Chloride (4 mg/mL) | 15.27 | NA |
| Leucovorin calcium (10 mg/mL), SBE-β-CD (75 mg/mL) + Sodium Chloride (4 mg/mL) | 17.91 | NA |
| Leucovorin calcium (10 mg/mL), SBE-β-CD (10 mg/mL) | 7.9 | NA |

Conclusion: High concentration of SBE-β-CD results in good saturation solubility at 2-8° C. However, as the required saturation solubility was around 14-15 mg/mL, there is no need to use higher concentrations of SBE-β-CD considering its potential nephrotoxicity. Low concentration of SBE-β-CD results in a lower solubility of leucovorin calcium API than the targeted saturation solubility window. Therefore, the optimized concentration of SBE-β-CD in this experiment was 50 mg/mL.

Example 4

A freeze-thaw study was conducted to evaluate the stability and crystallization resistance of the formulation of the present invention compared to a reference or comparative formulation. Both formulations were subjected to repetitive thermal stress cycles—each cycle consisting of freezing at −20° C. for 24 hours followed by thawing at 2-8° C. for 24 hours. This sequence was repeated across a total of 10 cycles to mimic harsh storage or shipping conditions and assess the propensity for crystallization.

The comparative formulation, which contained leucovorin calcium at a concentration of 10 mg/mL and sodium chloride at 8 mg/mL (without any cyclodextrin derivative), remained physically stable and visually clear for up to 5 freeze-thaw cycles. However, from the 6th cycle onward, signs of physical instability began to appear, including white flakes that dissolved upon shaking, followed by transparent undissolved particles by the 7th cycle. By the 10th cycle and beyond, the formulation exhibited persistent transparent particles, small white flakes, and needle-shaped crystalline fibers which clearly indicating crystallization.

In contrast, the formulation of the present invention, which included 10 mg/mL leucovorin calcium, 50 mg/mL of sulfobutyl ether β-cyclodextrin (SBE-β-CD), and 4 mg/mL sodium chloride, demonstrated superior stability under identical conditions. This formulation remained physically clear and free from crystallization up to 14 freeze-thaw cycles.

These results highlight the critical role of the cyclodextrin derivative in enhancing the physical stability of leucovorin calcium formulations, particularly under extreme temperature cycling.

Example 5

Stability studies of the formulations of the present invention were conducted at various pH as per standard procedure. The results of the studies are described below in Table 5.

TABLE 5

| | | DEGRADATION IMPURITIES | | | | | |
|---|---|---|---|---|---|---|---|
| S. No | pH | Impurity A (%) NMT 2 % | | Impurity F (%) NMT 1 % | | Total Impurities (%) NMT 2.5% | |
| Acceptance Criteria | | Initial | 2-8° C.—12 M | Initial | 2-8° C.—12 M | Initial | 2-8° C.—12 M |
| 1 | 7.0 | 0.018 | 0.46 | 0.041 | 1.26 | 0.44 | 2.2 |
| 2 | 7.5 | 0.020 | 0.55 | 0.030 | 0.56 | 0.42 | 1.7 |

TABLE 5-continued

| | | DEGRADATION IMPURITIES | | | | | |
|---|---|---|---|---|---|---|---|
| S. No | pH | Impurity A (%) NMT 2 % | | Impurity F (%) NMT 1 % | | Total Impurities (%) NMT 2.5% | |
| Acceptance Criteria | | Initial | 2-8° C.—12 M | Initial | 2-8° C.—12 M | Initial | 2-8° C.—12 M |
| 3 | 8.0 | 0.018 | 0.58 | 0.024 | 0.11 | 0.40 | 1.28 |
| 4 | 8.5 | 0.018 | 0.72 | 0.024 | 0.15 | 0.33 | 1.64 |

Conclusion: As evident from the above table, impurity levels at the time of preparation of composition for Impurity A and Impurity F and total are within desired limits. The levels of degradation Impurities A, F and total impurities were within the limits when stored at about 2° C. to about 8° C. for at least 12 months, at pH levels of about 7.5 to 8.5.

Example 6

Two types of formulations were prepared with the same excipients as disclosed in the exemplary formulations of present invention. The formulations were prepared by processes differing from each other in the sequence pH adjustment and were subjected to stability studies under standard conditions. Table 2 represents the result of stability study conducted on the formulation prepared by process wherein leucovorin calcium was added after pH adjustment to optimum range and is presented as below:

Sodium chloride→Tromethamine→Betadex Sulfobutyl Ether Sodium→pH adjustment→leucovorin calcium addition→Volume makeup Table 6 below represents the result of stability study conducted on the formulation prepared by process wherein leucovorin calcium was added before pH adjustment to optimum range and is presented as below:

Sodium chloride→Tromethamine→Betadex Sulfobutyl Ether Sodium→leucovorin calcium addition→pH adjustment→Volume makeup

TABLE 6

| Stability Study Result of Formulation | | | | | | | |
|---|---|---|---|---|---|---|---|
| Test parameters | Acceptance | | 2-8° C. | | | 25° C. ± 2° C. | |
| description | Criteria | Initial | 1 month | 3 month | 6 month | 1 month | 3 month |
| Description | A clear, colorless to yellow color solution | Clear colorless solution | Clear colorless solution | Light pale-yellow Color solution | Light pale-yellow Color solution | Clear colorless solution | Light pale-yellow Color solution |
| pH | 8.0-8.5 | 8.12 | 8.13 | 8.16 | 8.04 | 8.11 | 8.16 |
| Osmolality | NMT 600 | 384 | 385 | 382 | NP | 384 | 383 |
| Assay | 90-120% | 106.1 | 104.4 | 102.3 | 103.3 | 104.2 | 101 |
| Related substance | | | | | | | |
| Impurity A | NMT 2.0% | 0.041 | 0.127 | 0.279 | 0.367 | 0.3 | 0.758 |
| Impurity F | NMT 1.0% | 0.049 | 0.061 | 0.210 | 0.322 | 0.369 | 0.718 |
| Any unspecified impurity | NMT 0.5% | 0.05 | 0.048 | 0.052 | 0.054 | 0.081 | 0.171 |
| Total impurities | NMT 2.5% | 0.34 | 0.38 | 0.9 | 1.18 | 1.018 | 2.047 |

Conclusion: As per stability data shown in Table 2 and Table 6, the formulation prepared by process wherein the pH was adjusted before addition of leucovorin calcium shows a more controlled impurity profile when stored under refrigerated conditions and at accelerated condition (25° C.±2° C. and 60%±5% RH) and hence the order of pH adjustment plays a role in stability of formulation.

While the present invention has been described in terms of particular embodiments and applications, in both summarized and detailed forms, it is not intended that these descriptions in any way limit its scope to any such embodiments and applications. It will be understood that many substitutions, changes and variations in the described embodiments, applications and details of the method and system illustrated herein and of their operation can be made by those skilled in the art without departing from the spirit of this invention.

What is claimed is:

1. An aqueous injectable formulation comprising:

an active ingredient consisting essentially of leucovorin calcium;

a water-soluble cyclodextrin derivative;

a complex of the leucovorin calcium and the water-soluble cyclodextrin derivative;

wherein the water-soluble cyclodextrin derivative is present at a concentration of from about 20 mg/mL to about 100 mg/mL;

wherein the water-soluble cyclodextrin derivative is selected from sulfobutyl ether β-cyclodextrin (SBE-β-CD), hydroxypropyl β-cyclodextrin (HP-β-CD); and a combination thereof;

wherein the leucovorin calcium is present at a concentration of from about 5 mg/mL to about 25 mg/mL;

wherein the weight ratio of the leucovorin calcium to the cyclodextrin derivative is from about 1:4 to about 1:10;

wherein the pH of the formulation is between about 6.5 to about 8.5;

wherein the osmolality of the formulation is from about 200 mOsm to about 600 mOsm;

wherein the formulation remains substantially free from crystallization for at least 6 months when stored at a temperature of from about 2° C. to about 8° C., and for up to 3 months at a temperature of about 25° C.±2° C.; and wherein the formulation is suitable for intravenous or intramuscular administration without reconstitution or dilution.

2. The formulation according to claim 1, further comprising a co-solubilizer; a buffering agent; a pH adjusting agent; a pharmaceutically acceptable vehicle; or a combination of two or more thereof.

3. The formulation according to claim 2, wherein the co-solubilizer comprises sodium chloride and is present at a concentration of about 4 mg/mL to about 12 mg/mL of total formulation.

4. The formulation according to claim 2, wherein the buffering agent is selected from the group consisting of: tromethamine; a phosphate buffering agent; an acetate buffering agent; a citrate buffering agent; and a combination of two or more thereof.

5. The formulation according to claim 4, wherein the buffering agent is tromethamine and is present at a concentration of about 5 mg/mL to about 10 mg/mL.

6. The formulation according to claim 2, wherein the pH adjusting agent comprises hydrochloric acid and/or sodium hydroxide.

7. The formulation according to claim 2, wherein the pharmaceutically acceptable vehicle comprises water for injection.

8. An aqueous injectable formulation comprising:

(a) about 10 mg/mL of leucovorin calcium;

(b) about 50 mg/mL of a cyclodextrin derivative selected from SBE-β-CD; HP-β-CD; and a combination thereof;

(c) about 5 mg/mL of a co-solubilizer;

(d) about 7 mg/mL of a buffering agent;

(e) a pH adjusting agent comprising hydrochloric acid and/or sodium hydroxide; and (f) water for injection;

wherein the leucovorin calcium is the only active ingredient;

wherein the pH of the formulation is from about 8.0 to about 8.5;

wherein the osmolality of the formulation is about 350 mOsm;

wherein the formulation remains substantially free from crystallization for at least 6 months when stored at a temperature of from about 2° C. to about 8° C., and for up to 3 months at a temperature of about 25° C.±2° C.; and wherein the formulation is suitable for intravenous or intramuscular administration without reconstitution or dilution.

9. The formulation according to claim 1, comprising:

not more than 2.0% of 4-amino benzoyl glutamic acid;

not more than 1.0% of 10-formyl dihydrofolic acid;

not more than 0.5% of an unspecified impurity; and not more than 2.5% of total impurities, all based on the weight of leucovorin calcium, and determined by high-performance liquid chromatography (HPLC).

10. The formulation according to claim 8, comprising:

not more than 2.0% of 4-amino benzoyl glutamic acid;

not more than 1.0% of 10-formyl dihydrofolic acid;

not more than 0.5% of an unspecified impurity; and not more than 2.5% of total impurities, all based on the weight of leucovorin calcium, and determined by high-performance liquid chromatography (HPLC).

11. The formulation according to claim 1, wherein the formulation does not contain a preservative or an antioxidant.

12. The formulation according to claim 8, wherein the formulation does not contain a preservative or an antioxidant.

13. The formulation according to claim 1, wherein the formulation remains clear and free from crystallization after being subjected to at least 10 cycles of freezing at about −20° C. for 48 hours followed by thawing at about 25° C. for 48 hours.

14. A pharmaceutical product comprising:

a formulation according to claim 1, wherein the formulation is filled into an amber single-dose container configured to receive a fill volume of 5 mL, 35 mL or 50 mL.

15. A method of treating a condition related to high-dose methotrexate therapy, comprising administering the formulation according to claim 1, to a subject in need thereof, wherein the condition is selected from:

(a) osteosarcoma;

(b) toxicity or adverse effects of impaired methotrexate elimination; and (c) inadvertent overdose of folic acid antagonists.

16. A method of treating megaloblastic anemia due to folic acid deficiency, comprising administering the formulation according to claim 1, to a subject in need thereof, wherein the subject is unable to undergo oral folinic acid therapy.

17. A method of treating advanced colorectal cancer, comprising administering the formulation according to claim 1, in combination with 5-fluorouracil to a subject in need thereof.

18. A method of treating a condition related to high-dose methotrexate therapy, comprising administering the formulation according to claim 8, to a subject in need thereof, wherein the condition is selected from:

(a) osteosarcoma;

(b) toxicity or adverse effects of impaired methotrexate elimination, and (c) inadvertent overdose of folic acid antagonists.

19. A method of treating megaloblastic anemia due to folic acid deficiency, comprising administering the formulation according to claim 8, to a subject in need thereof, wherein the subject is unable to undergo oral folinic acid therapy.

20. A method of treating advanced colorectal cancer, comprising administering the formulation according to claim 8, in combination with 5-fluorouracil to a subject in need thereof.

* * * * *